(12) United States Patent
Edwards et al.

(10) Patent No.: US 10,045,694 B2
(45) Date of Patent: Aug. 14, 2018

(54) INTEGRATED DIAGNOSTIC DEVICE

(71) Applicant: LIA DIAGNOSTICS, INC., Philadelphia, PA (US)

(72) Inventors: Bethany Ann Edwards, Harveys Lake, PA (US); Frances Melina Dimare, St. Augustine, FL (US)

(73) Assignee: LIA DIAGNOSTICS, INC., Philadelphia, PA (US)

( * ) Notice: Subject to any disclaimer, the term of this patent is extended or adjusted under 35 U.S.C. 154(b) by 0 days.

(21) Appl. No.: 15/470,762

(22) Filed: Mar. 27, 2017

(65) Prior Publication Data
US 2017/0280999 A1    Oct. 5, 2017

Related U.S. Application Data

(63) Continuation of application No. 14/706,159, filed on May 7, 2015, now Pat. No. 9,606,116.

(60) Provisional application No. 61/996,978, filed on May 11, 2014.

(51) Int. Cl.
| | | |
|---|---|---|
| *G01N 21/75* | (2006.01) | |
| *A61B 5/00* | (2006.01) | |
| *A61B 5/145* | (2006.01) | |
| *G01N 33/493* | (2006.01) | |
| *A61B 5/20* | (2006.01) | |
| *A61B 10/00* | (2006.01) | |

(52) U.S. Cl.
CPC ............... *A61B 5/00* (2013.01); *A61B 5/145* (2013.01); *A61B 5/14507* (2013.01); *A61B 5/20* (2013.01); *G01N 33/493* (2013.01); *A61B 5/207* (2013.01); *A61B 10/007* (2013.01)

(58) Field of Classification Search
CPC .......... G01N 33/493; A61B 5/00; A61B 5/20; A61B 5/145; A61B 5/14507; A61B 10/007; A61B 5/207
See application file for complete search history.

(56) References Cited

U.S. PATENT DOCUMENTS

| | | |
|---|---|---|
| 5,605,161 A | 2/1997 | Cross |
| 5,866,675 A | 2/1999 | Ahmed |
| 6,403,298 B1 | 6/2002 | Lee et al. |
| | (Continued) | |

FOREIGN PATENT DOCUMENTS

| | | |
|---|---|---|
| CN | 102639245 A | 8/2012 |
| EP | 0321237 B1 | 10/1992 |
| | (Continued) | |

OTHER PUBLICATIONS

Guidelines for Assessing the Flushability of Disposable Nonwoven Products, Third Edition, Aug. 2013, Copyright 2013 INDA and EDANA.

(Continued)

*Primary Examiner* — Dennis White
(74) *Attorney, Agent, or Firm* — Troutman Sanders LLP (57) ABSTRACT

A flexible, integrated, urine-based diagnostic device designed such that one or more diagnostic channels are integrated into the body of the device. Each diagnostic channel is designed to contain an immunoassay to detect the presence of a selected analyte so that the device can return a visible readout indicating the presence of the analyte. The flexibility of the device aids the user in the sample collection process.

19 Claims, 4 Drawing Sheets

(56) References Cited

U.S. PATENT DOCUMENTS

| | | |
|---|---|---|
| 6,673,982 B1 | 1/2004 | Chen |
| 8,278,109 B2 | 10/2012 | Nazareth |
| 2005/0136529 A1 | 6/2005 | Yang |
| 2005/0182376 A1* | 8/2005 | Fleming ............ A61F 13/47209 604/385.01 |
| 2006/0040405 A1 | 6/2006 | Charlton |
| 2008/0095912 A1 | 4/2008 | Loughran |
| 2008/0103414 A1 | 5/2008 | Song |
| 2008/0286879 A1 | 11/2008 | Lee |
| 2009/0061534 A1 | 3/2009 | Sharrock |
| 2009/0263854 A1 | 10/2009 | Jacono |
| 2010/0030173 A1 | 2/2010 | Song |
| 2013/0162981 A1 | 6/2013 | Emeric |

FOREIGN PATENT DOCUMENTS

| | | |
|---|---|---|
| WO | 1995008761 A1 | 3/1995 |
| WO | 00/65348 A2 | 11/2000 |
| WO | 2008080220 A1 | 7/2008 |
| WO | 2013178739 A1 | 12/2013 |

OTHER PUBLICATIONS

Wang, Morphology and Entrapped Enzyme Performance in Inkjet-Printed Sol-Gel Coatings on Paper, 26 Chemistry of Materials, 2014, pp. 1941-1947, American Chemical Society.

Mogera, Ultrafast Response Humidity Sensor Using Supramolecular Nanofibre and its Application in Monitoring Breath Humidity and Flow, Scientific Reports 4, Feb. 17, 2014.

\* cited by examiner

INTEGRATED DIAGNOSTIC DEVICE

CROSS-REFERENCE TO RELATED APPLICATIONS

The present application is a continuation application of U.S. application Ser. No. 14/706,159, filed May 7, 2015, now allowed, which claims priority to U.S. provisional patent application No. 61/996,978, filed on May 11, 2014. The contents of these applications are incorporated herein by reference in their entirety.

BACKGROUND OF THE INVENTION

Urine-based diagnostic devices in their generic form are used in home and clinical settings for both men and women to test for a wide variety of conditions and analytes that may be present in urine and other body fluids. The devices have been developed to provide for quick, accurate, and easy-to-use testing for people untrained in the field.

Existing devices typically comprise at least two parts: a rigid structure to serve as a support for the device, and a testing strip which carries out the test itself. Such devices use rigid body structures, an imprecise specimen collection method (sometimes requiring counting from the user), singular abstract readout per testing strip (in non-electronic devices), and implied landfill disposal. Urine-based diagnostics usually fall into the categories of midstream (device is held in flowing stream of fluid), dip (device is held in stationary fluid sample), and cassette (dropper is used to add fluid sample).

The increasing popularity and complexity of these devices have led to a number of problems. Those of skill in the art will appreciate that a test format remains desirable that integrates the entirety of the device, including the user interface, collection portion, and testing portion, into a single format. This would help to simplify the manufacturing process as well as to improving the ease-of-use of the device. Additionally, the increase in complexity of existing devices has enabled such devices to give electronic readouts of the results at the expense of increasing cost and the requirement of battery operation. Those of skill in the art would appreciate a testing format in which the device is able to give both a positive and negative indicator without the use of electronic components remains desirable. This solution would be particularly important as it aids the user experience, reduces cost, simplifies manufacture, and avoids the use of expensive, and non-biodegradable electronic components. The user experience could be even further improved by using a visual readout that has a clearer indication than the current non-electronic devices in the market that typically use one or more lines to indicate the result which are often difficult to interpret.

Because these diagnostic devices are often used to obtain sensitive test results, discretion is typically an important priority for the user. There are a number ways to improve test discretion. For discretion while carrying the device, it would be desirable to create a device that is not only small, but is able to be folded to compact form without damaging the device itself. Additionally, discretion at disposal can be particularly important where one would not want the device to be found. Therefore, a test format that is completely flushable or water dispersible would be advantageous. A flushable, water dispersible, or biodegradable device would also be desirable as it would reduce dependency on landfill systems.

Ease-of-use is also important for these types of at-home testing devices which are typically used by untrained people. Typical hand-held devices are rigid and require aiming of urine on the part of the user, which tends to be particularly difficult for females. Other devices in the field attempt to solve this problem by allowing the user to dip the test in a sample, or attach the device to a toilet. Those of skill in the art would recognize that a device that could aid in sample collection and testing without first collection of the sample in a separate container, or attaching the device to an object for collection, would be advantageous to ease the user experience.

BRIEF SUMMARY OF VARIOUS EMBODIMENTS OF THE INVENTION

The present invention is directed to urine-based diagnostic tests and testing devices that address the above-mentioned and other needs in the art. One embodiment of the device is designed to create a single, integrated, testing device that comprises the user interface, collection portion, and testing portion that increases the simplicity of manufacturing and ease-of-use of the device. In this embodiment, one or more diagnostic channels are integrated into the device material. Each diagnostic channel includes an immunoassay for reacting with an analyte in a sample. Additionally, the device itself is flexible such that can be adjusted to aid in the collection of urine.

Other embodiments of the device include one or more channels having a sandwich immunoassay, a competitive immunoassay, or both a competitive and sandwich immunoassay. In other embodiments, the competitive and sandwich immunoassays are able to give either a positive or negative visual readout to the user. Other embodiments of the device can be flushable, water dispersible, or biodegradable to both reduce reliance on landfills as well as aiding in keeping the test discrete. In other embodiments, the device can also be foldable to aid in keeping the device discrete as well as to aid in transportation of the product. In other embodiments, the readout of the device is displayed by text, graphic designs, or symbols to aid in the ease-of-use. Other embodiments of the device may further include an embossed pattern on the collection portion of the device to aid in collection and to direct flow of the sample. In further embodiments, the collection portion of the device includes a perforation such that the soiled portion of the device can be removed after sample collection without affecting the results of the test.

BRIEF DESCRIPTION OF THE DRAWINGS

The above-mentioned and other advantageous features of the invention will be apparent from the following detailed description in connection with the attached drawings, of which.

DETAILED DESCRIPTION

The various embodiments of the present invention are designed as integrated diagnostic devices wherein the structure, user interface, collection portion, and test portion form a single, easy-to-use, and simple to manufacture testing device.

Figure 1:
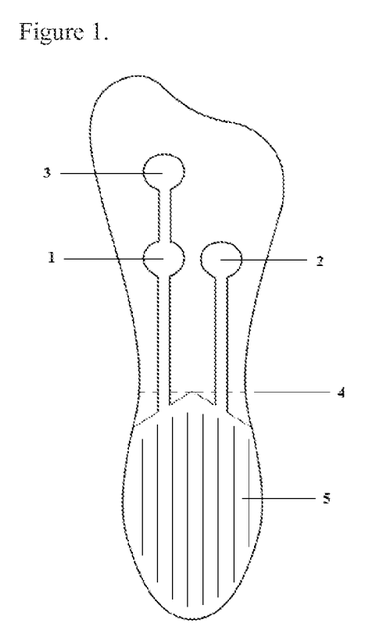
FIG. 1 is a perspective view of one embodiment of the device which includes a volume indicator, positive indicator, control indicator, tear-line, and embossed collection pad.

One embodiment of the device is illustrated in FIG. 1. This embodiment is an integrated device that comprises a diagnostic channel with an immunoassay 1, a urine volume indicator 2, a control indicator 3, a perforation 4, and an embossed collection pad 5. In one embodiment, the device uses microfluidic techniques as the channel system of the diagnostic assay which allows the system to be a single manufactured object with the user interface and structure. The device integrates these attributes into a single material such that the piece that the user holds, uses, or urinates on is materially integrated with the microfluidic channels and diagnostic assay. The arrangement of the immunoassay 1, urine volume indicator 2, and control indicator 3, in FIG. 1 is not the only one contemplated and should not be limited to this layout. A control indicator 3 is included to provide a visible indication that the test has run.

In the embodiment illustrated in FIG. 1, the immunoassay can be designed to test for various analytes. For example, in one embodiment the immunoassay could be designed to test for the hormone hCG which would allow the device to return a result with respect to whether the user is pregnant. However, the device can be designed to test for any number of analytes present in urine including, but not limited to, hCG-H and various drugs (such as cocaine, THC, or amphetamines), glucose, ketones, luteinizing hormone, or hemoglobin. Depending on the analyte chosen, the device can be designed to test for various conditions, diseases, or other information including the presence of sexually transmitted diseases, diabetes, pregnancy, kidney disease, or cancers.

The immunoassays being used in the various embodiments can be designed in a number of different ways. For example, the immunoassay can be designed as a "sandwich" assay or a "competitive" assay. Additionally, the immunoassays can be structured to test in a lateral flow or vertical flow format. The type of assay being used will depend on the desired function of the device. For example, persons of skill in the art would recognize that a "sandwich" assay would be useful if one desired the device to indicate the presence of an analyte above a predetermined concentration while a "competitive" assay would indicate when the desired analyte is absent at a predetermined level.

The immunoassays can be adhered to the non-woven material of the device in a number of ways. A simple method for accomplishing this would be to add a mixture of the biorecognition agents directly to the device in the desired format and then drying the mixture to adhere it to the device. The biorecognition agent depends on the analyte being tested for and can include antibodies, hormones, or other chemicals that detect the target analyte. This method of drying antibodies to the device has the added benefit of simplicity. However, other methods can be used, such as various printing techniques. An example would be to use ink-jet printing, which a person of ordinary skill would find as useful because, among other reasons, it is a non-impact technique. One example of inkjet printing that can be used is through the use of Sol-Gel. See e.g., Jingyun Wang, et. al., Morphology and Entrapped Enzyme Performance in Inkjet-Printed Sol-Gel Coatings on Paper, 26 *Chem. Mater.* 1941 (2014), incorporated herein by reference. However, other application techniques of Sol-Gel can be used such as dot-matrix printing, screen printing, coating, automated pipettes, stamping, or spraying.

The channels for these immunoassays may also be created in a number of ways. One simple method for creating the channels is through the use of impact techniques where indentations are created in the material in which the immunoassays can be added. In these embossing techniques, the indentations form channels that direct liquid to flow through to the immunoassays. Additionally, embossing techniques can be used to create barriers by varying the density of the device material whereby denser, hydrophobic channel walls are created that direct the flow of the sample through the channels. Another way that the channels can be created is through printing methods. For example, inkjet printable sol-gel materials can be used to create hydrophobic barriers for these channels in some embodiments. See e.g., Jingyun Wang, et. al., Morphology and Entrapped Enzyme Performance in Inkjet-Printed Sol-Gel Coatings on Paper, 26 *Chem. Mater.* 1941 (2014).

One of skill in the art would recognize a number of advantages in integrating the testing channels and immunoassays into the device itself. This technique avoids the use of nitrocellulose test strips which are used in many devices in the market. By avoiding the use of the nitrocellulose test strips, and integrating the entirety of the device into a single material, the manufacturing process is simplified. Additionally, the nitrocellulose test strips are not flushable, which is a significant barrier to creating an entirely flushable strip.

In the embodiment demonstrated in FIG. 1, the urine volume indicator 2 provides for a visual indication of the sufficiency of the sample. Persons of skill in the art would recognize this feature as advantageous over ways of indicating volume sufficiency in existing applications in which the user is expected to count anywhere from five to 30 seconds in his or her head to understand when the device has a sufficient volume of fluid sample. Having a volume indicator 2 integrated into the device also avoids the use of electronic equipment within the device to indicate when a sufficient fluid level is achieved. There also exist devices that have color changing properties to indicate that the device is in contact with fluid, but such devices do not indicate if the appropriate volume is achieved. The volume indicator 2 in FIG. 1 can be achieved in a number of ways including through the use of a hydrochromic ink portion as part of the urine-based diagnostic device that is designed to complete its hydrochromic transformation when enough fluid sample of the urine is achieved for the diagnostic to perform optimally. Hydrochromic inks react to fluid by modifying the appearance of their color. The design of this in relation to the device could, in some embodiments, be linear and communicate as part of the user interface. Its transformation from one color to another would indicate as a visual tool to the user that a satisfactory amount of fluid sample is on and within the diagnostic device. While hydrochromic ink may be used in a preferred embodiment of the device, other volume indicators can be used including hydrochromic paint, a chromatic assay, an acid/base reactive test, dispersing an ink or paint when wet, the appearance of an element when the testing material becomes translucent or transparent when wet, or through the use of chemically sensitive materials. One example of a chemically sensitive material is the use of humidity sensitive nanofibers. See e.g., Mogera, U. et. al., Ultrafast Response Humidity Sensor Using Supramolecular Nanofibre and its Application in Monitoring Breath Humidity and Flow, 4 Sci. Rep. 4103 (2014), incorporated herein by reference.

The embodiment depicted in FIG. 1 also includes a perforation 4. This perforation is designed such that the soiled portion of the device used to collect the sample can be discarded by the user while awaiting the results without affecting the readout. A person of skill in the art would recognize this as advantageous for a number of reasons including reducing the size of the test to be discarded to aid in flushability as well as allowing the user to discard the soiled portion of the device while awaiting results for sanitary reasons.

The embodiment in FIG. 1 further comprises an embossed collection pad 5. This collection pad 5 is designed in such a way to increase the surface area of the collection portion of the device and aid in the flow of sample to the testing portion of the device. To increase flow to the testing portion of the device, it would be beneficial for the channels in the embossed pattern to be oriented vertically, i.e., parallel to the immunoassay channels. However, the embossed pattern can be designed in a number of ways to adjust the time it takes for the sample to reach the channels. By adjusting the embossed pattern, one could design the device to return a fast result without having the sample move so fast that it washes the biorecognition agents out of the immunoassays. In this way, one can control the speed at which the device returns the result.

In other embodiments of this invention, the entirety of the device can be flushed or is water dispersible which provides an optional layer of privacy for users not wanting their results to enter the landfill or recycling bound municipal waste systems. Flushability is determined by the device's form and materiality, though there are multiple combinations of the two. The constraints of the device could be characterized as being small enough in depth and width to pass through all standard plumbing. In an exemplary embodiment, the material is formed from cellulose fibers in compressed or non-woven format and may include binding materials like polyvinyl alcohol, although other types of materials can be used. The non-woven formats can be created by a number of different processes including either wet laid or air laid operations. Wet laid and air laid nonwoven techniques are well known in the art. See e.g., EP0321237 B1 incorporated herein by reference. Additionally, the cellulose pulp fibers can be hydroentangled in order to prevent degradation during use of the device while still maintaining flushability. However, while cellulose mixtures are preferred, the invention is not limited to this material as long as the selected material satisfies the flushability requirements. One such suitable material for use in this application is available from Suominen Corporation under the trade name HYDRASPUN™. The combination should dissolve to the standards and guidelines set out in the "Guidelines for Assessing the Flushability of Disposable Nonwoven Products: A Process for Assessing the Compatibility of Disposable Nonwoven Products with Plumbing and Wastewater Infrastructure. Third Edition. August 2013. © 2013 INDA and EDANA."

In another embodiment of the invention, the device may be adjusted or is flexible for the purposes of user interaction and personalization, packaging, and transportation. Persons of skill in the art would recognize that in order for women to urinate on a midstream diagnostic device, some level of aiming on the part of the user is necessary, creating an opportunity for misuse or confusion on the part of the user. Culturally, women are not expected to aim their urine stream in many cases and a flexible solution gives opportunity for user adjustment and user personalization to accommodate the flow and directionality of their urine stream. The action of collecting urine by a midstream device can be simplified by a more dynamic design that allows for greater user control. The flexibility of the device can be adjusted based on the material being used. For example, non woven materials can be made more or less flexible based on the way in which the fibers are bound, the way in which the material is manufactured, and the additives added to the cellulose materials. More specifically, increased rigidity of the nonwoven material can be accomplished through a number of methods including but not limited to compression molding or the addition of water dispersible hardeners such as wet strength resins. In some embodiments, the device can be highly flexible, while in others the device can be more rigid in nature. For example, based on the non-woven material or techniques being used, the device can be designed to be adjusted into a desirable form—by the user or others—prior to use whereupon it may keep its form through the sample collection process. In this way, the form of the device can be personalized depending on the user.

Figure 5:
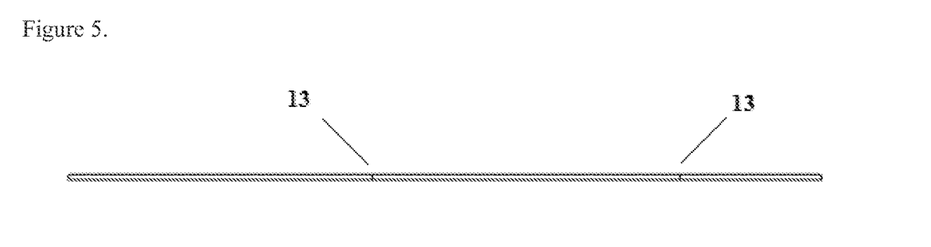
FIG. 5 is a side view of one embodiment of the device where the device is opened flat.
Figure 6:
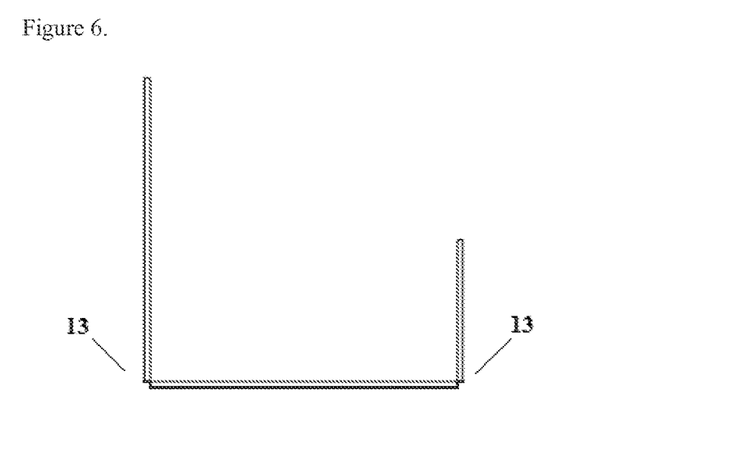
FIG. 6 is a side view of one embodiment of the device where the device is halfway folded.
Figure 7:
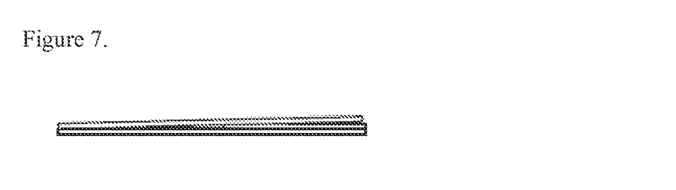
FIG. 7 is a side view of one embodiment of the device where the device is completely folded.

In another embodiment of the invention, the device is foldable. By being foldable, the device may be more easily packaged and transported. Additionally, a foldable device aids in discretion as it can reduce the size of the device allowing for discrete carrying. A foldable embodiment of the device is demonstrated in FIGS. 5, 6, and 7. In these examples, the device has two fold lines 13 such that the device's surface area can be reduced for more discrete carrying and for packaging. However, there can be any number of fold lines depending on what size folded device is desired. Additionally, the integrated manner in manufacturing this device into a single material is what allows the foldable property to be possible without affecting the integrity of the device.

Figure 2:
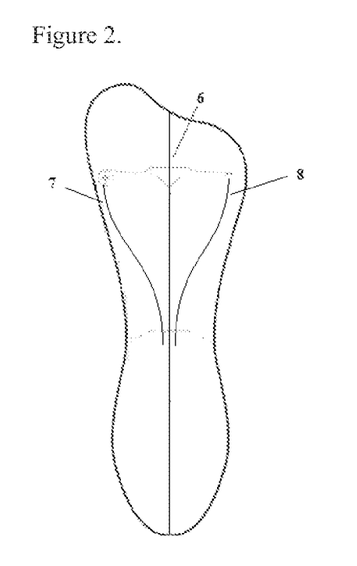
FIG. 2 is a perspective view of one embodiment of the device in which two immunoassays are integrated into the device in order to give a positive or negative readout.

FIG. 2 depicts another embodiment of the device in which the device utilizes both a "regular" or "sandwich" assay 7 as well as a "competitive" assay 8 as well as a volume indicator 6. A "regular" or "sandwich" assay 7 is used to show a chromatic visual readout when the specified element or hormone is present. These can take on a number of formats including lateral flow or vertical flow tests. Persons of skill in the art would recognize that this regular assay, also called an enzyme-linked immunosorbent assay (ELISA), is commonly used in current testing devices, such as many pregnancy testing kits currently on the market. In this regular assay, a biorecognition agent is used to bind to a selected analyte in order to give a visual readout when it is present at a predetermined concentration. In this context, the chromatic visual readout would not occur if the specified element or hormone were not present. In a "competitive" assay 8, this scenario is reversed from the perspective of the user. An additional phase to the assay is included that contains a form of the specified element or hormone with a conjugated enzyme. Should the specified element or hormone exist in the collected urine sample, it may travel through the channels of the assay "competing" with the modified elements with conjugated enzymes for antibodies with which to bind. In this scenario, the color change would not occur and the visual readout would not be displayed to the user. Should the specified element or hormone not exist in the collected urine sample, the modified elements with conjugated enzymes would have no "competition" for antibodies with which to bind and would produce a color changing visual readout for the user. This embodiment of the invention includes the feature of having both of these types of assays coexisting in a single urine-based diagnostic device. One example of this would be in a pregnancy test that a pregnant woman would get a visual diagnostic readout indicating the presence of the hormone hCG (human chorionic gonadotrophin) yet a non-pregnant woman would also get a visual diagnostic readout indicating the lack of hCG.

Figure 8:
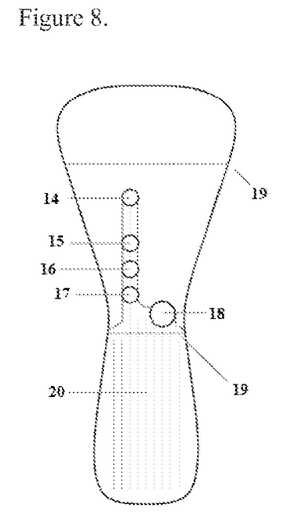
FIG. 8 is a perspective view of an embodiment of the device that includes a control, a first immunoassay, a second immunoassay, and a third immunoassay in the same channel, a volume indicator, two fold lines, and an embossed collection pad.

FIG. 8 depicts another embodiment in which the device utilizes a control 14, a first immunoassay 15, a second immunoassay 16, and a third immunoassay 17 in the same channel, a volume indicator 18, two fold lines 19, and an embossed collection pad 20. In this embodiment, the multiple immunoassays are configured to test for different analytes. For example, the first immunoassay can be designed to detect for hCG at a predetermined level, the second immunoassay can be designed to detect for glucose at a predetermined level, and the third can be designed to detect for luteinizing hormone. In this way, the device can test for the presence of three different analytes using a single sample. However, this embodiment of the invention is not limited to this number of immunoassays or these analytes. The device can be configured with a plurality of immunoassays to test any number of analytes in order to give the desired number and type of results.

In further embodiments, the plurality of immunoassays can be designed to test for multiple levels of an analyte. For example, the device can be configured with three immunoassays each testing for a different concentration of hCG, such as 25,000 mIU/ml, 7,000 mIU/ml, and 25 mIU/ml. In this example, the device could indicate not only a positive result for pregnancy, but could approximate the period of time the user has been pregnant. By testing for multiple volumes of an analyte, the user could also be given an approximate range for the amount of analyte in the sample. The number of immunoassays being used in the device and the levels being tested for can be varied based on what type of information the device needs to return—a higher number of immunoassays testing for smaller analyte volume intervals may return more accurate estimations of the volume of the target analyte in the sample.

Figure 3:
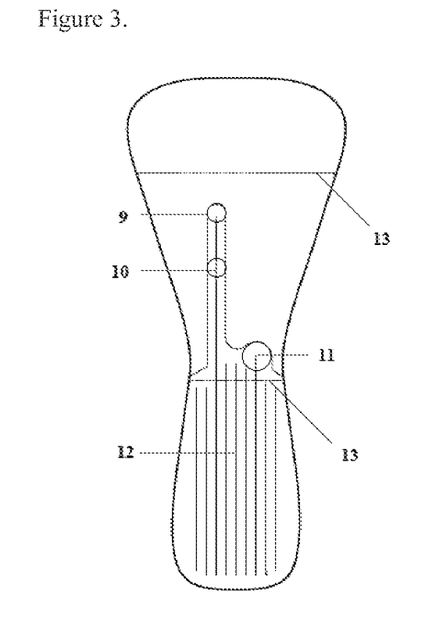
FIG. 3 is a perspective view of one embodiment of the device that includes a positive readout, a control indicator, a volume indicator, an embossed collection area, and two fold lines.

FIG. 3 depicts another embodiment of the device which utilizes a control indicator 9, a positive readout 19, a volume indicator 11, an embossed collection area 12, and fold lines 13. In this embodiment, the control indicator 9 and positive readout 10 are situated in a linear arrangement. The volume indicator 11 is designed to allow the user to know when sufficient sample volume is achieved. The embossed collection pad 12 aids in directing flow to the channels. The fold lines 13 enable the user to fold the device to a smaller size for easier and more discrete carrying.

Figure 4:
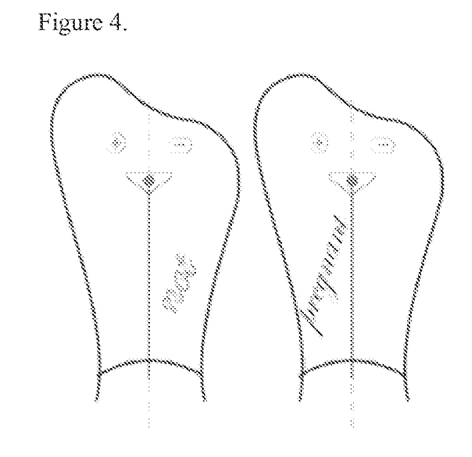
FIG. 4 is a perspective view of a portion of one embodiment of the device wherein the test results are given using written word readouts.

FIG. 4 depicts another embodiment of the device in which the diagnostic readout is represented using words or language. Persons of skill in the art would recognize that this adds a level of clarity and ease-of-use over existing devices which rely on lines, squares, or patterns or on electronic materials to provide a readout in written language. The device includes a feature that allows for a non-electronic device to have a word or language readout of the diagnostic results. The microfluidic channels are designed in a way that the color changing portions of the diagnostic assay are positioned into a pattern resembling words. One example would be for the device to have the antibodies in a designed channel so that, if the diagnostic were positive, a pregnancy could convey this in the written word "Pregnant".

Figure 9:
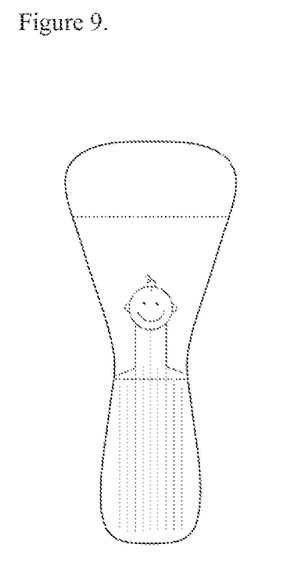
FIG. 9 is a perspective view of an embodiment of the device wherein the test results are given using a graphic design.

FIG. 9, depicts another embodiment of the device in which the visual readout is displayed using a graphic design or other pictorial representation. By using a recognizable graphic representation of the results of the test, the ease-of-use of the device is enhanced. This design is achieved by designing the microfluidic channels is the form of the desired graphic. In the embodiment displayed by FIG. 9, the device utilizes a baby's face to indicate a positive pregnancy test result. However, other graphics or pictorial representations can be used based on what type of analyte the device is configured to detect.

The various embodiments of the invention are designed for an untrained person (although not limited to use by such a person) to use the device to test for a selected analyte or condition. The user of the device, after adjusting its flexible form to aid in sample collection, can add the urine sample to the collection portion of the device, possibly by urinating directly onto the device. The sample may then travel through the testing portion of the device before the device returns a visual result.

What is claimed is:

1. A device for use with a fluid sample, comprising a water-dispersible diagnostic device having a diagnostic channel, wherein the diagnostic channel is formed of a water-dispersible material and includes a biorecognition agent capable of detecting an analyte in the fluid sample.

2. The device of claim 1, further comprising a body formed of a water-dispersible material, wherein the diagnostic channel is positioned in the body.

3. The device of claim 1, wherein the water-dispersible material is a flushable material.

4. The device of claim 1, wherein the device is biodegradable.

5. The device of claim 2, wherein the diagnostic channel and the body are composed of non-woven cellulose.

6. The device of claim 2, further comprising an embossed pattern on the body or the diagnostic channel.

7. The device of claim 1, wherein the biorecognition agent is an immunoassay reagent.

8. The device of claim 1, wherein the biorecognition agent comprises multiple biorecognition agents, each capable binding a different analyte, if present, in the fluid sample.

9. The device of claim 2, wherein the diagnostic channel and the body are comprised of the same water-dispersible material.

10. The device of claim 1, wherein the device is a hand-held device.

11. The device of claim 1, wherein the water-dispersible material comprises a nonwoven material.

12. A device for use with a fluid sample, comprising a water-dispersible diagnostic device capable of detecting an analyte in the fluid sample, wherein the water-dispersible diagnostic device has a diagnostic channel formed of a water-dispersible material, and wherein the water-dispersible diagnostic device includes a biorecognition agent in the diagnostic channel.

13. The device of claim 12, further comprising a body formed of a water-dispersible material, wherein the diagnostic channel is positioned in the body.

14. The device of claim 12, wherein the water-dispersible material is a flushable material.

15. The device of claim 12, wherein the device is biodegradable.

16. The device of claim 12, wherein the water-dispersible material comprises a nonwoven material.

17. A diagnostic device of the lateral flow, vertical flow, or colormetric type, including a biorecognition agent in a diagnostic channel and capable of detecting an analyte in a fluid sample,
characterized
in that the diagnostic device is comprised entirely of a water-dispersible material.

18. The lateral or vertical flow diagnostic device of claim 17, wherein the lateral or vertical flow diagnostic device comprises an immunoassay device.

19. The lateral or vertical flow diagnostic device of claim 17, wherein the water-dispersible material is a flushable material.

* * * * *